United States Patent
Schwarz

(10) Patent No.: US 6,631,000 B1
(45) Date of Patent: Oct. 7, 2003

(54) DEVICE AND PROCEDURE FOR THE QUALITY CONTROL OF IN PARTICULAR FINISHED SURFACES

(75) Inventor: Peter Schwarz, Geretsried (DE)

(73) Assignee: BYK Gardner GmbH (DE)

( * ) Notice: Subject to any disclaimer, the term of this patent is extended or adjusted under 35 U.S.C. 154(b) by 156 days.

(21) Appl. No.: 09/692,603

(22) Filed: Oct. 19, 2000

(65) Prior Publication Data (65)

(30) Foreign Application Priority Data

Oct. 20, 1999 (DE) .......................... 199 50 588

(51) Int. Cl.$^7$ .............................. G01N 21/01
(52) U.S. Cl. .................. 356/445; 250/227.29
(58) Field of Search ................ 356/445, 446, 356/405, 406, 425; 250/227.23, 227.29

(56) References Cited

U.S. PATENT DOCUMENTS 4,917,495 A  *  4/1990  Steenhoek .................. 356/328
5,387,977 A  *  2/1995  Berg et al. ................ 250/227.3

* cited by examiner

Primary Examiner—Georgia Epps
Assistant Examiner—Richard Hanig

(57) ABSTRACT

The present invention relates to a device and a procedure for the quality control of in particular finished surfaces wherein the device comprises at least one illuminating means having at least one light source, its light directed at a predetermined angle to the measurement surface. A plurality of at least three measuring means is provided, whereby each of said measuring means is directed at a different predetermined angle to the measurement surface and receives a portion of the light reflected from said measurement surface. Each measuring means comprises at least one photosensor which emits an electrical measurement signal which is characteristic of the light received by said measuring means. A control and evaluation means having at least one processor means and one memory means controls the measurement sequence, evaluates the measurement results and derives therefrom a parameter which characterizes the surface. An output means serves for the outputting of parameters or measurement results.

20 Claims, 4 Drawing Sheets

DEVICE AND PROCEDURE FOR THE QUALITY CONTROL OF IN PARTICULAR FINISHED SURFACES

DESCRIPTION

The present invention relates to a device and a procedure for the quality control of in particular finished surfaces. In numerous products, the quality or the visual properties of its surface become an important characteristic for the overall appearance of the product. Thus, in order to achieve a high reproducibility during production, retouching or repair work on objects, quality control measurements are carried out on the products to determine one or several parameters (such as for example: color, gloss, haze, orange peel, etc.).

Particularly with finished surface's, but not limited solely thereto, their visual properties may change depending upon viewing angle, respectively angle of illumination. Such surfaces are called goniochromatic.

Examples of such surfaces are those with effect, metallic or pearl lustre finishes, coated surfaces as well as interference color surfaces, or even synthetic surfaces having inlaid transparent particles and other such similar surfaces.

Finished surfaces having inlaid metal particles may exhibit, for example, FLOP effects so that a change in color dependant upon the viewing angle may be observed. Such effects may be induced, for example, by aluminum particles inlaid in the surface and which then act as mirrors.

In order to offer consumers products featuring new colors, new finishes are developed which are able to exhibit specific qualities.

In many effect finishes, there is a particular viewing angle at which a change in parameters occurs. Should a surface be observed at a slightly lesser angle, a first impression of color may, for instance, be noted, while a second impression of color, which may conceivably differ considerably from the first impression of color, may be noted upon scanning or measuring at a slightly greater angle.

Measuring devices which illuminate a measurement surface at an angle and which measure the reflected light at two fixed angle ranges in order to determine the color of a surface to be examined under these two scanning angles are known from the prior art. Furthermore, goniometric measuring devices are also known in the prior art with which, for example, a surface is illuminated at a fixed angle and a photosensor is trammed across the entire angle range in order to obtain the surface color as a function of the scanning angle.

However, goniometric devices have the disadvantage that in order to determine color function, the sensor must be trammed over the entire angle range during each measurement and a mechanical decalibrating of the device cannot always be excluded.

It is the task of the present invention to provide a device and a procedure of the type as indicated above to enable a quality control of surfaces and finished surfaces in particular.

Another aspect of the task of the present invention is to provide a device which can determine at least one visual property of a surface, including of those surfaces which may also have been given new finishes or other such similar treatments.

SUMMARY OF THE INVENTION

This task is solved in accordance with the present inventive device and method as described herein.

Preferred embodiments of the invention constitute the subject matter of the subclaims.

A device according to the present invention for the quality control of especially finished surfaces comprises an illuminating means having at least one light source. The light radiated from said illuminating means is directed to the measurement surface at a predetermined angle. A plurality of at least three, preferably at least five measuring means are furthermore provided, which each receive at least a portion of the light reflected by the measurement surface. Each measuring means has at least one photosensor which emits at least one electrical measurement signal, whereby said electrical measurement signal is characteristic of the light received by the measuring means.

The inventive device furthermore has at least one control and evaluation means provided with at least one processor and at least one memory means in order to control the measurement sequence, evaluate the measurement results, and derive a parameter from the measurement signals which characterizes the surface. An output means serves to display, respectively forward, the measurement results.

The device according to the present invention has numerous advantages:

Arranging each of the plurality of measuring means in the inventive device at a different angle to the measurement surface enables the evaluation means to derive a parameter which is characteristic of the surface from the measurement signals of the individual measuring means.

Preferably at least one characteristic parameter is determined for the measured surface; this parameter may be its color, gloss, haze, orange peel or distinction of image. It is moreover possible that two or three different parameters can be determined and/or that, for example, at least one parameter each may be determined from respectively two, three or all measuring means.

Especially preferred is determining the color parameter of the measurement surface whereby it is possible that a set of color characteristics are determined in that, for example, each measuring means determines one color characteristic. In a preferred embodiment of the invention, a plurality of retaining means are provided in the device upon each of which a measuring means is disposed. Especially preferred is that the number of retaining means is greater or identical to the number of measuring means so that, for example, ten retaining means are provided whereby measuring means are disposed upon five of these ten retaining means.

A greater number of retaining means relative to the number of measuring means is highly advantageous because this enables changing the position of one measuring means from a first retaining means to a second retaining means upon which no other measuring means has been disposed.

With this type of device, the individual positions of the measuring means can be changed essentially at any time which enables the device to be adapted to changed conditions.

The retaining means serve to hold or support the measuring means, respectively parts thereof, and are preferably realized as conventional retaining means as known in the prior art.

In a preferred embodiment of the present invention, the angle spacing between at least three adjacent retaining means is in each case identical and especially preferred is that essentially all the angle spacings of adjacent retaining means are essentially identical. For example, more than 30 retaining means are disposed across a 180° range of angles in the present embodiment, the spacings between said means in each case amounting to 5°, whereby a greater angle spacing can also be given between a first area of the retaining means and a second area of the retaining means. It is likewise possible that the aggregate of retaining means are distributed across, for example, three angle ranges in that the angle spacings from one to the next are identical, whereby greater angle spacings are found between the individual areas.

This embodiment is particularly advantageous. Positioning the retaining means for instance at a 3° or 5° spacing from one another enables setting the angle at which a measuring means receives a portion of the light reflected from the surface at small increments. Should the retaining means be arranged during the actual manufacturing of the device, a measuring means can be brought from one retaining means onto another retaining means with relatively low expenditure.

In a preferred embodiment of the present invention, at least one measuring means comprises an optical photoconductor means and a spectral means, whereby the optical photoconductor means receives a portion of the light reflected from the measurement surface and conveys same to the spectral means. In this embodiment, the predetermined angle at which the measuring means is directed to the measurement surface corresponds to the angle at which in this case the optical photoconductor means is directed to the measurement surface, while parts of the measuring means, such as for example the spectral means, may then be aligned at any chosen angle. The disposing of optical photoconductor means in at least one measuring means (preferably in essentially all measuring means) is of great advantage as this enables the providing of a small optics block in the device which is the size of, for example, a matchbox or a paperback book. This in turn keeps the overall size of the device small enough so that it can be used portably by the user.

In a preferred embodiment of the present invention, at least two, preferably essentially all the measuring means, receive essentially simultaneous measurement signals during the measurement of the surface, fundamentally ruling out any distortions in the measurement results such as those due to, for example, temporal fluctuations in the radiated light intensity of the illuminating means. This embodiment has the further advantage of reducing the overall measurement time required since the light received can be analyzed concurrently in the various measuring means.

In another preferred embodiment of the present invention, at least two, preferably all of the measuring means receive the measurement signals basically one after the other. A configuration of this type grants the advantage that the intensity of surface illumination can be varied for the individual measuring means so that, for example, the intensity of illumination can be increased for measurements employing measuring means arranged at an angle to the surface at which only low light is reflected, while inversely the intensity of illumination can be decreased for those measuring means arranged at angle ranges at which a great deal of light is reflected. This enables operating the sensors at a consistently high dot resolution so that a high signal-to-noise ratio may be obtained.

In a further preferred embodiment of the present invention, a filter means is arranged in the path of radiation between the light source and at least one photosensor. The filter means changes the spectral characteristics of the incident light according to the specific filter properties in such a manner that a spectral characteristic of the conveyed light approaches that of a predetermined spectral distribution.

Utilizing of a filter means enables the spectral distribution of the light used for the measurement to be adapted to specific stipulations.

In a further preferred embodiment of the present invention, said predetermined spectral distribution is a standard distribution which exhibits a constant intensity, for example in at least one wavelength band, or a distribution which exhibits, for example, the C light type standard, the D65 light type standard, the A light type standard or other such similar standards. A measurement conducted can thus be illuminated, respectively measured, directly under standard conditions.

In another preferred embodiment, a spectral measurement characteristic is proportional to a predetermined spectral distribution, wherein same may correspond, for example, to a constant value across the relevant wavelength band or to a Gaussian distribution or to the spectral visual sensitivity of the human eye. The spectral measurement characteristic is thereby determined as a product of the measurement surface incident light and the spectral sensitivity of the photosensor.

The adaptation of the spectral distribution or the spectral measurement characteristics to predetermined spectral distributions is highly advantageous. When the spectral distribution is adapted to the sensitivity of the human eye, it is then possible to adapt measurement conditions to the average human being. On the other hand, if the spectral measurement characteristic is adapted to an essentially constant spectral distribution, measurement accuracy is increased since a higher signal-to-noise ratio is obtained.

In a preferred embodiment of the present invention, the illuminating means has at least two light sources, whereby said light sources are configured preferably as conventional light sources as known in the prior art. It is possible to use, for example, conventional or halogen light bulbs, fluorescent and/or semi-conductor light sources. It is especially preferred for at least two of the light sources of said illuminating means to exhibit a different spectral characteristic. The second light source may then emit light, for example particularly in those bands of radiation in which the first light source emits at only low intensity or none at all, so that the spectral distribution of the intensity of radiation of both light sources exhibits less pronounced minima. Especially preferred when utilizing at least two light sources is that at least one of said light sources is a light-emitting diode. The use of light-emitting diodes as light sources in the illuminating means is highly advantageous since light-emitting diodes are subject to less aging than conventional thermal sources of radiation and since they continue to radiate at a relatively stable light intensity over time. In another preferred embodiment of the present invention, a control measuring means is provided in the illuminating means which is fed, at least intermittently, a part of the light emitted from the illuminating means. Since fluctuations in light intensity can be taken into account, a control measuring means which determines a standard gauge for the light emitted from the illuminating means allows for increasing the reproducibility of the measurement.

In a preferred embodiment of the present invention, at least one photosensor (preferably all) has a number of photosensitive elements which are preferably arranged adjacent to one another. Especially preferred is the configuration of a row of photodiodes or a CCD array. It is highly advantageous, particularly when utilizing spectral means in the measuring means, to provide a plurality of photosensitive elements on one or on each photosensor, since the spectral means can then split the received light according to wavelength and thus feed light of different wavelengths to the individual photosensitive elements of the photosensors so that the spectral distribution of the received radiation can be determined.

Especially preferred is the configuring of the spectral means of the measuring means as diffracting optical elements, whereby same may be configured as transmitting as well as also reflecting elements.

In a further preferred embodiment of one or all of the previously described embodiments, at least one temperature measuring means is disposed in immediate proximity to at least one light source and/or at least one photosensor, provided for determining the characteristic temperature of each respective light source, respectively photosensor, in order to enable a temperature-corrected determination of said at least one parameter.

Especially preferred in this case is that one or several photosensors are disposed with such a temperature measuring means so as to grant increased measurement reproducibility and accuracy by means of the temperature-corrected determination of the measurement results.

The temperature measuring means can hereby particularly also be the electric component itself, especially with semiconductor components such as conventional photosensors. This enables deriving the component's temperature from the determination of open-circuit voltage, amperage or other electrical characteristic. Using such a component itself to determine its temperature is highly advantageous because due to the slight time difference between temperature measurement and light measurement (respectively as regards light sources, between the temperature measurement and the light radiation), such a determination is very reliable as there is no, or only negligibly slight thermal capacities to distort the determination of temperature in dynamic processes.

The inventive procedure makes use of one of the previously described configurations of the measuring device having a plurality of measuring means, whereby adjacent measuring means preferably have the same angle spacing to one another. Said device is provided with preferably at least ten, especially preferred with up to 60 or more measuring means, each aligned at different predetermined angles to the measurement surface.

The inventive procedure is utilized preferably for the determining at least of one, preferably two, three, four, five or more scanning angles of a surface type.

When measuring with a first measuring device which is preferably designed especially for laboratory operation, parameters can be determined for the surface to be examined from a number of angles. By evaluating said plurality of parameters, typically one, two, three or more scanning angles can be determined which characterize the surface type to be examined.

In the case of so-called effect finishes, these are for example a nacreous or a FLOP effect angle, meaning an angle at which, for example, a color change is observable.

In addition to the determining of at least one characteristic angle for the surface type to be examined, a measuring means is disposed in a second measuring device at a specific angle respective said first measuring means, respectively a measuring device is built to realize this angle.

Preferably, the first measuring device (laboratory device) selects at least three different angles in the inventive procedure and transmits same to the second measuring device (field measuring device), so that three different measuring means are aligned in said second measuring device at the corresponding angles.

In a preferred embodiment of the inventive procedure, the second measuring device has a plurality of retaining means, said plurality being greater than the number of measuring means in the second measuring device. It is preferable that the angle spacing between adjacent retaining means is essentially the same. Subsequent to the determining of a characteristic angle with the first measuring device, the measuring means of the second measuring device may then be brought into the corresponding position.

In a preferred embodiment of the inventive procedure, the arrangement of the retaining means of the second measuring device (field measuring device) is identical to the arrangement of the retaining means in the first measuring device (laboratory device).

It is preferred that the field measuring device encompasses essentially identical optical conditions as in the laboratory device. This ensures a simple transferability of the geometrical relationships and enables the attaining of a high reproducibility to the measurement results. The retaining means of the hand-held or field measuring device may also be configured differently from the retaining means of the laboratory device. It is likewise also possible that the illuminating means and the measuring means of the hand-held measuring device are not identical to those of the laboratory device since greater demands are often placed on laboratory measuring devices, for example with respect to precision.

It is likewise particularly preferred that the optics block on which the retaining means are arranged is essentially the same in both measuring devices, whereby the production tolerance for the first measuring device may be more exacting than the production tolerance for the second measuring device.

A further advantage of the inventive measuring device is that essentially no movable elements are used in said measuring device.

BRIEF DESCRIPTION OF THE DRAWINGS

Further advantages, features and application possibilities of the present invention will now be specified in the following description of embodiments in conjunction with the drawings, which show.

DETAILED DESCRIPTION OF THE INVENTION

A first embodiment will now be described with reference to FIG. 1.

Figure 1:
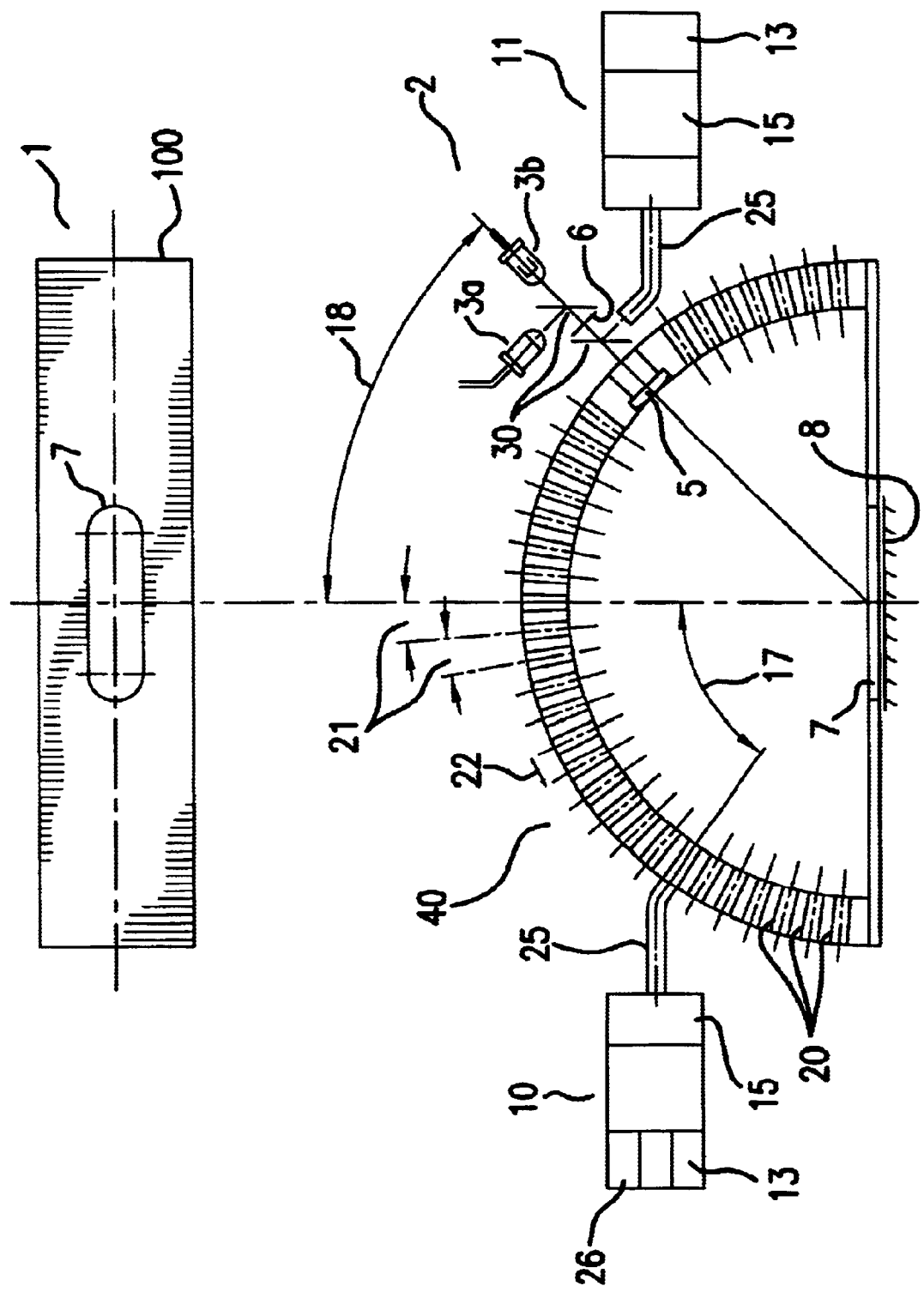
FIG. 1: the principal construction of a device according to a first embodiment of the present invention.

Based on the orientation according to FIG. 1, an underview of housing 100 of the inventive measuring device 1 is illustrated on the left side. Light from illuminating means 2 is emitted through opening 7 on the underside of housing 100 onto measurement surface 8 of the surface to be examined and the reflected light is received by measuring means 10.

The right side of FIG. 1 shows a sectional cut through the schematically represented measuring device 1.

An optics block 40 is disposed in housing 100 of measuring device 1, which exhibits a semi-circular cross-section in the figure's illustrated plane.

Measuring devices corresponding to this embodiment are particularly well suited as laboratory measuring devices in which a high degree of precision is often desired.

The measuring means comprises illuminating means 2 having light sources 3a and 3b. Light source 3a in the present embodiment is configured as a light-emitting diode, while light source 3b is a thermal emitter and specifically a halogen light source. It is however likewise possible that both light sources as represented are light-emitting diodes. In this case, two spectrally differing light sources are employed in order to raise the spectral intensity of the aggregate radiated light in those spectral bands in which the first or second light source emits at only low intensity. This thus allows for obtaining a more uniform intensity of radiation across the relevant band of the spectrum, in this case the visible part of the spectrum. In the present embodiment, the two light sources are arranged essentially rectangularly to one another and emit light onto a first beam splitter 30, which is aligned at 45° to both light sources so that the light thus forwarded is composed of portions of the light radiated from the first and from the second light source.

A filter means 6 is arranged in the successive path of radiation, which influences particular spectral bands by means of reflection or absorption in a specific manner so as to adapt the spectrum of the transmitted light to a predetermined spectrum. By adapting the emitted spectrum to a predetermined spectral characteristic, a higher degree of measurement accuracy can be achieved since, for example, specifically those spectral bands with particularly high intensity can be damped such that the difference between maximum and minimum spectral intensity is low and consequently the signal-to-noise ratio increased.

A second beam splitter 30 is then additionally arranged in the path of radiation and conveys a part of the radiated light over an optical photoconductor 25 to measuring means 11 which includes a spectral means 15 and a photosensor 13. Measuring means 11 is a control measuring means provided for controlling the intensity and spectral distribution of the light radiated onto measurement surface 8. The measurement results returned by said control measuring means may in turn be used as a form of feedback for regulating the light sources 3a and 3b in order to stabilize the intensity and the spectral distribution of the radiated light.

The light passing through the second beam splitter 30 is focused onto measurement surface 8 by lens 5. It is also possible to parallelize this light.

A portion of the light reflected by measurement surface 8 impinges a light receiving means of optical photoconductor 25, which is a part of measuring means 10, at an angle 17 to the normal of the measurement surface.

Optical measuring means 10 in the present embodiment comprises a fiber optic photoconductor 25, which in this example has a diameter of 125 μm and is configured as a single fiber. It is however likewise possible that a cluster of fibers having a differing diameter is employed.

The photoconductor is fixed on the light-receiving end of optical fiber 25 by means of a metallic sleeve or ferrule and is held in place via retaining means 20 of optics block 40. Retaining means 20 has a bore into which optical fiber 25 with its sleeve is inserted. The fiber is held in the bore of the retaining means by, for example, pressure fit, adhesive, a bolted connection or such similar securing coupling. In the present embodiment, the bores of retaining means 20 are aligned with respect to the measurement surface, while the photosensors 13 may be arranged virtually at will, since the light received by fibers 25 will be transported to their positions. In the present embodiment, a plurality of such optical measuring means 10 are arranged all aligned in one plane in optics block 40. Said plane is defined by the rays of light directed to the measurement surface and reflected therefrom.

Optics block 40 extends semi-circularly into said plane and has retaining means 20 for measuring means 10 arranged at uniform angle spacings around its circumference. Axes through retaining means 20 are in each case aligned to the measurement surface 8, respectively the point of measurement.

For the sake of clarity and overview, only one measuring means is illustrated in FIG. 1. It is however to be pointed out that such a measuring means 10 may be arranged in each of the retaining means 20, so that the light reflected from the surface at different directional angles may be received by different measuring means 10. In the present embodiment, the angle spacing 21, respectively 22, between a first measuring means 10 and a second measuring means 10 is 5° so that up to 36 measuring means may be arranged over the semi-circular circumference of measuring device 1 whereby no measuring means are arranged in the small angle range in which the illuminating means is disposed. In this area, the angle spacing between a measuring means on one side of the illuminating means and a measuring means on the other side of the illuminating means is somewhat greater and amounts to 20° in the present embodiment.

Taking 0° to the measurement surface normal as a basis, measuring means are arranged symmetrically every 5° on both sides, up to an angle of 85°. When one takes the omitted three into account (at the position of the illuminating means), a total number of 32 measuring means ensues.

Such a plurality of measuring means is especially advantageous since the various different measuring means receive and analyse light reflected from the surface at essentially all ranges of angles.

Each measuring means 10 preferably comprises a fiber optic photoconductor 25, a spectral means 15, as well as a photosensor 13, which in the present embodiment is configured as a diode row and has a plurality of photosensitive elements 26.

Spectral means 15 in the present embodiment is an optical transmission grid which breaks down the light emitted from fiber 25 to spectral means 15 into its spectral components and conveys same to photosensor 13, wherein different wavelengths reach different photosensitive elements 26. This allows, upon receiving the signal of photosensor 13, that the spectral distribution ensues with the light received by measuring means 10. This can be employed in conjunction with the spectral distribution of the spectrum received by control measuring means 11 for determining the color of measurement surface 8.

The spectral means are small spectrometers and preferably micro spectrometers which are preferably the size of a paper clip or a matchbox, thus consequently enabling a compact and portable measuring device.

In the present embodiment, each of the plurality of measuring means 10 determines one color of the measurement surface 8 so that subsequent to taking a measurement, one color parameter is given for each different measurement angle 17 for the surface to be examined 8. By comparing the individual color values, it is then possible to determine individual angles 17 which characterize the surface type to be examined. Particularly with so-called color effect finishes, color changes dependent upon the angle of their viewing can be noted.

In the case of new finishes, such color changes can occur at other angles than has previously been known. For this reason, a laboratory measuring device such as given in the present invention is highly advantageous because a color parameter determination can be made at any of various different angles. Analyzing the individual color parameters determined thus allows for the establishing of scanning angles suited to characterize such a type of finish, type of surface respectively.

It is then possible to transfer the one, two, three, four, five or even more selected angles to a second measuring device, in that a corresponding number of measuring means 10 are arranged at the corresponding angles in said second measuring device. When such a surface type is then subsequently measured with the measuring device, the user will then in practice receive sufficient information in order to determine, for example, the color parameter of such surfaces. Usually, e.g in the case of retouching or repairing of damaged products, the corresponding product's surface color composition is determined, wherein this transpires by means of a measurement at, for example, three different angles. The color composition can be determined with the measured color parameters and a database and the appropriate color can then be produced or mixed.

This conventional procedure, which measures at two or three specifically set angles, can fail in the case of new finishes, since new finishes may necessitate a measurement at other angles. Color shade, for example, may only be correct at certain viewing angles, while an observer will perceive a different impression of color at other angles.

The inventive laboratory measuring device can simply, quickly and reliably determine the essential scanning angles for a measurement of color. In contrast, goniometric measurement procedures in which a sensor is, for example, trammed across the relevant range of angles, have the disadvantage that measurement results can be distorted due to mechanical decalibrations.

In the embodiment according to FIG. 1, angle 18, at which the light radiated from illuminating means 2 is directed to measurement surface 8 relative the surface normal, is 45°. It is however also possible to illuminate the surface to be measured at an angle of 0° to the normal of measurement surface 8 or at another angle as defined by measurement standards.

Figure 2:
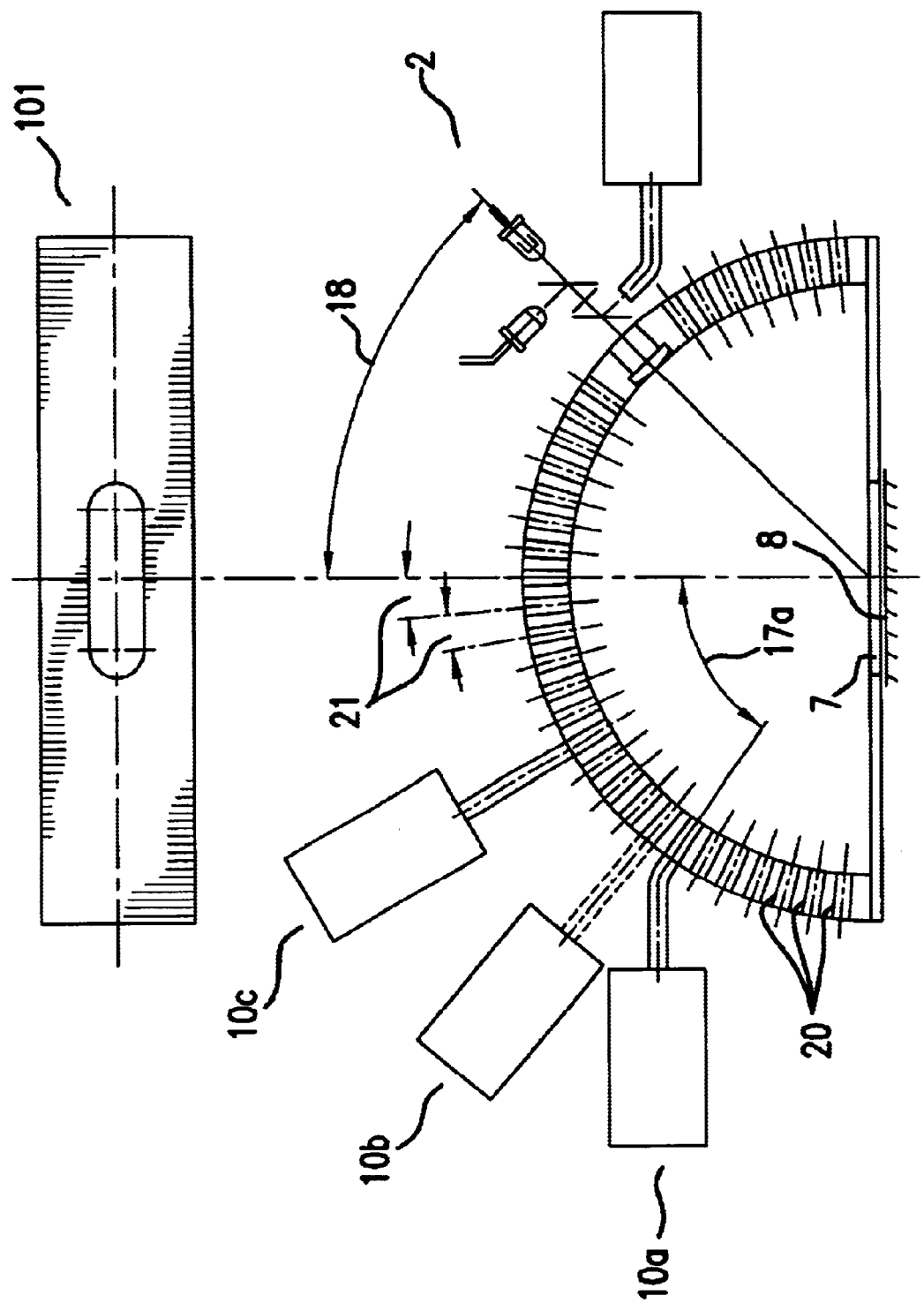
FIG. 2: the principal construction of a device according to a second embodiment of the present invention.

FIG. 2 represents a second embodiment of a measuring device according to the present invention, wherein the housing 101 of the measuring device is shown on the left side of FIG. 2 and the right side illustrates a sectional cut through such a measuring device.

Components which are identical or similar to components represented in the first embodiment have been given the same reference numerals in the embodiment according to FIG. 2 and an explicit explanation thereof has been omitted.

In the present embodiment, the inventive device likewise has an illuminating means 2 which radiates light onto the measurement surface to be examined.

In like manner as in FIG. 1, a plurality of retaining means 20 is provided in optics block 40, each arranged at angle spacing 21.

In contrast to the embodiment represented by FIG. 1, the embodiment represented in FIG. 2 is disposed with only a few measuring means 10a, 10b and 10c, whereby the number of measuring means may also amount to three, four, five, six, seven or more. It is preferred to have between three and six measuring means.

Each of these measuring means, respectively light-receiving optical fibers 25, is directed at a different angle to measurement surface 8 and hence receives a different part of the light reflected from said measurement surface.

Although each of measuring means 10a, 10b and 10c are arranged in retaining means 20, an angle spacing from a measuring means 10a to a second measuring means 10b may be smaller than an angle spacing between a measuring means 10b and a measuring means 10c, because in the example as illustrated, a total of three retaining means remain vacant between measuring means 10b and measuring means 10c.

In the present second embodiment of the inventive device, angles 17, respectively 17a, at which the individual measuring means are arranged, are determined through measuring with a laboratory measuring device in accordance with the first embodiment. In this manner, a device according to the present invention in accordance with the first embodiment can determine the relevant angles 17, 17a, 17b as well as 17c at which the individual measuring means of the measuring device must be arranged relative the surface to be measured in accordance with the second embodiment.

Although the retaining means and the measuring means in the second embodiment have been provided with the same reference numerals as in the first embodiment, the individual components do not have to be identical; it is thus also possible to make use of differently configured retainers and different measuring and illuminating means in the measuring devices according to the first and the second embodiments. It is however preferable to realize essentially corresponding optical conditions and particularly preferable to realize identical optical conditions in the hand-held measuring device according to the second embodiment and in the laboratory measuring device according to th e first embodiment.

In a second step, the positions of the measuring means of the measuring device according to the second embodiment can be changed, so that angles 17a, 17b and 17c, at which the individual measuring means are arranged, may be adjusted. Such an adaptation may conceivably be carried out by the user himself or also by the manufacturer.

Providing a plurality of retaining means in the inventive measuring device allows for a measuring device which is especially flexible in its application. The spacing 21, respectively 22, from the first retaining means to the second retaining means in this case can amount to between 1° and 15°, and preferably 3°, 5°, 6° or 10°.

Figure 3A:
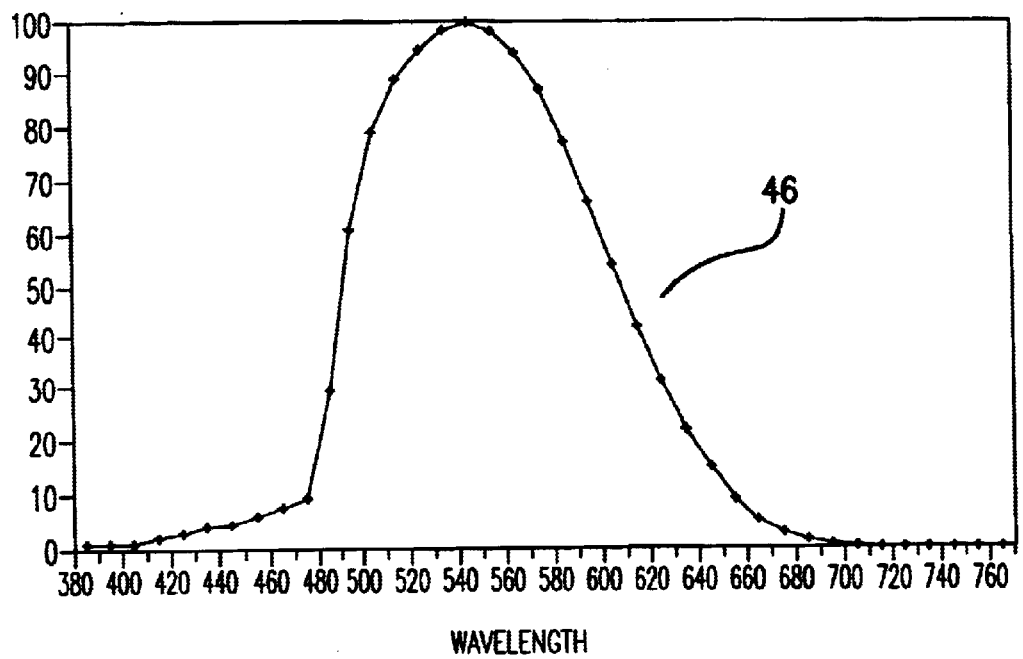
FIG. 3a: the spectral distribution of radiated light.
Figure 3B:
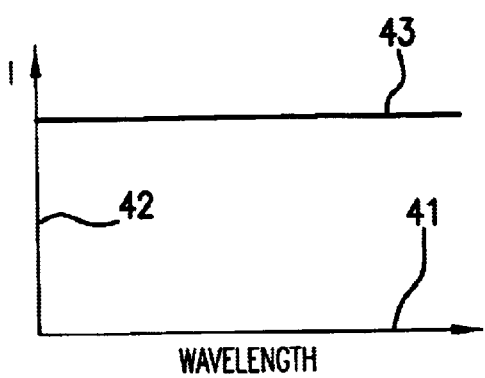
FIG. 3b: the spectral distribution of intensity of light received by a measuring means.
Figure 3C:
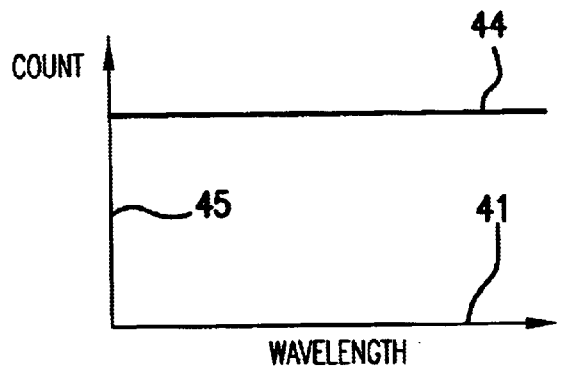
FIG. 3c: a spectral signal distribution of a sensor signal.

In FIGS. 3a, 3b and 3c, different spectral distributions are represented as could be given with the embodiments according to FIG. 1 and FIG. 2.

FIG. 3a illustrates the relative spectral intensity of the light radiated onto the surface subsequent to passage through spectral filter 6, whereby spectral distribution 46 corresponds fundamentally to spectral eye sensitivity $V_\lambda$, so that the light emitted from illuminating means 2 is essentially proportional to the spectral sensitivity of a human eye.

FIG. 3b represents the spectral intensity 43 of the light impinging photosensor 13 at wavelengths 41 when an ideally reflecting surface is being measured. In this embodiment, one or more filter element(s) 6 are arranged in the path of radiation between the illuminating means and the photosensor in order to achieve a spectral distribution of the incident light on photosensor 13 which is as constant as possible. Among the advantages of such a configuration is that a deviation in spectral intensity can be identified immediately.

The spectral signal distribution 44 of a photosensor 13 at wavelengths 41 in a further embodiment is represented in FIG. 3c, whereby one or more filter element(s) can be provided in filter means 6 to specifically influence the spectral distribution of the light emitted from illuminating means 3. Then, upon illumination of an ideally reflective surface, one of the spectral signal distributions 44 approaching the spectral signal distribution of photosensor 13 can be determined.

The deliberate influencing of the spectral intensity in accordance with the embodiment according to FIG. 3c is also especially advantageous in that an essentially constant signal 44 is determinable across all relevant wavelengths 41 in the case of an ide ally reflective surface. The term "essentially" is to be understood here as also encompassing possible fluctuations of up to 50%. Even in the case of still larger deviations, the spectral distribution can still be regarded as being essentially constant, if one considers that signal ratios between minimal and maximum ranges of 1:2, 1:3, 1:10, 1:100 or even greater are possible without filter means 6.

A relative constant spectral signal distribution of sensor signal 44 allows for the signal-to noise ratio to assume as large a value as possible, in turn increasing measurement accuracy. The embodiments in accordance with FIG. 1 and FIG. 2 may comprise such filter elements, respectively filter means 6, as described with regard to FIGS. 3a, 3b and 3c.

Figure 4:
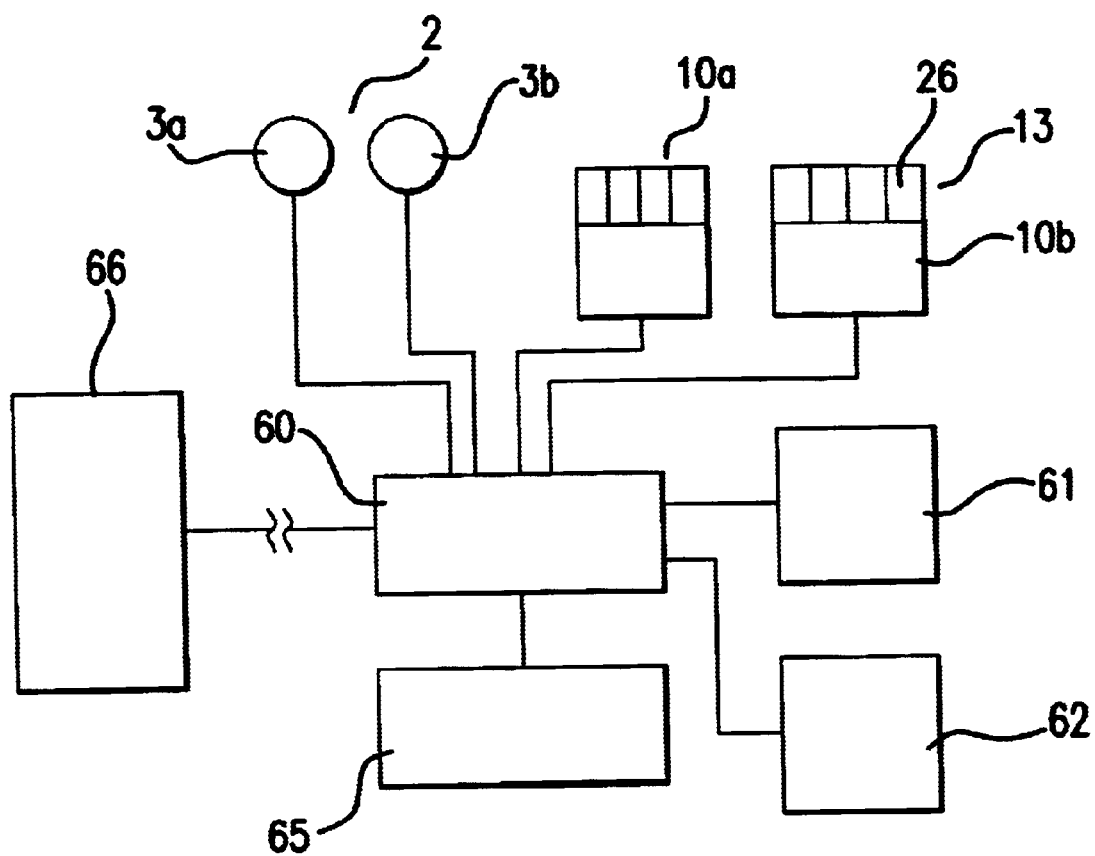
FIG. 4: a basic technical circuitry configuration of all previously described embodiments.

FIG. 4 illustrates the basic technical circuitry configuration of all previously described embodiments.

A control and evaluation means 60 comprises a processor means 60 and serves to control the measurement sequence by means of a program stored in memory means 61. The measurement results are likewise stored in memory means 61 and can additionally be transferred to an external computer 66. An input device 62 is provided for controlling the measuring device and an output means 65 is likewise provided, configured as an LCD display in the present embodiment. It is preferred that output means 65 comprises an electric interface for conveying the measurement results.

Processor 60 controls the illuminating means and their light sources 3a, 3b and records the measurement signals received by measuring means 10a, 10b for further processing. Each of measuring means 10a, 10b comprises one photosensor 13 each including photosensitive elements 26, their photosignals each being individually determinable.

Should a measuring device be employed as a laboratory device for the determining of the characteristic scanning angle for a new finish, a special program to this effect can be started via input means 62, which records the measurement signals of the plurality of measuring means 10 and stores same in memory means 61.

Subsequent to the determination of the individual color parameters of the corresponding measuring means, a number of characteristic parameters which characterize the surface type of the measured measurement surface are selected from all parameters as determined. The relevant angles are additionally determined and output to display 65 together with the parameters.

These angles can then be transferred to another measuring device. For example, measuring devices can be built in which these angles are provided. Or angles 17 are changed in a measuring device, for example, in that the measuring devices are arranged on other bores, respectively retaining means.

What is claimed is:

1. Device for the quality control of finished surfaces, comprising:
    at least one illuminating means having at least one light source that directs light at a predetermined angle to the measurement surface which is a part of the surface to be measured;
    a plurality of at least three measuring means, with each of said measuring means being directed at a respectively different predetermined angle to said measurement surface and receiving a portion of the light reflected from said measurement surface, and with each of said measuring means having at least one photosensor which emits an electrical measurement signal characteristic of the light received by said measuring means;
    at least one control and evaluation means provided for the control of the measurement sequence and the evaluation of the measurement results and which comprises at least one processor means and at least one memory means;
    an output means;
    wherein said evaluation means evaluates said measurement signals and derives therefrom at least one parameter which characterizes said surface; and
    wherein an angle spacing from a first retaining means to a second retaining means is essentially equal to an angle spacing from the second retaining means to a third retaining means.

2. Device according to claim 1, wherein said characterized parameter of said measurement surface is at least a color of said measurement surface.

3. Device according to claim 1, wherein at least one of said at least one characterized parameter is selected from among a group of parameters which consists of gloss, haze, orange peel, distinctness of image (DOI) and color of said measurement surface.

4. Device according to claim 1, wherein a plurality of retaining means is provided, with each respective measuring means arranged on one of said retaining means.

5. Device according to claim 4, wherein the number of said retaining means is greater or equal to the number of said measuring means.

6. Device according to claim 1, wherein all angle spacings between adjacent retaining means are identical.

7. Device according to claim 1, wherein said light received by at least one measuring means is conveyed to a spectral means via an optical photoconductor means.

8. Device according to claim 1, wherein at least two of the measuring means receives measurement signals simultaneously.

9. Device according to claim 1, wherein at least two of the measuring means receives measurement signals one after the other.

10. Device according to claim 1, wherein a filter means is provided arranged in the path of radiation between said light source and said photosensor and which changes a spectral characteristic of the incident light in accordance with predetermined filter properties such that a spectral characteristic of the conveyed light essentially approaches a predetermined spectral distribution.

11. Device according to claim 10, wherein said predetermined spectral distribution is a standard distribution which comprises a type of light taken from a group of light norm standards which consists of the C light type standard, the D65 light type standard and the A light type standard.

12. Device according to claim 1, wherein a spectral measurement characteristic which is a product of the spectral characteristic of the light radiated onto the measurement surface and the spectral sensitivity of the sensor is proportional to a predetermined spectral distribution.

13. Device according to claim 1, wherein said illuminating means comprises at least two light sources having different spectral characteristics, wherein at least one light source is configured as a light-emitting diode.

14. Device according to claim 1, wherein the light radiated from said illuminating means is at least partially conveyed at least intermittently to a control measuring means of said illuminating means.

15. Device according to claim 1, wherein at least one of said photosensors comprises a plurality of photosensitive elements, which are arranged adjacent to one another.

16. Device according to claim 1, wherein at least one temperature measuring means is disposed immediately proximate to at least one light source, and is provided for determining the characteristic temperature of each respective light source, in order to enable a temperature-corrected determination of said at least one parameter.

17. Device according to claim 1, wherein at least one temperature measuring means is disposed immediately proximate to at least one photosensor, and is provided for determining the characteristic temperature of each respective photosensor, in order to enable a temperature-corrected determination of said at least one parameter.

18. Method for the quality control of finished surfaces, employing:

a first measuring device comprising:
   at least one illuminating means having at least one light source which directs light at a predetermined angle to a measurement surface which is a part of the surface to be measured;
   a plurality of measuring means, whereby each of said measuring means is respectively aligned at a predetermined angle to said measurement surface and receives a portion of the light reflected from said measurement surface, and whereby each measuring means comprises at least one photosensor which emits an electrical measurement signal which is characteristic of the light received by said measuring means;
   at least one control and evaluation means comprising at least one processor means and at least one memory means, wherein said control means controls the measurement sequence and evaluates the measurement results and derives therefrom at least one parameter which characterizes said surface; and
   an output means for outputting at least said at least one parameter;

wherein the method comprises the steps of:
   a) bringing said first device into a position for measurement relative to a measurement surface of a surface type to be examined;
   b) radiating light onto the measurement surface to be examined by said at least one illuminating means;
   c) from said light reflected by said measurement surface, from substantially each of said plurality of measuring means, emitting a measurement signal and determining a parameter, with said parameter relative the respective measuring means being stored in a parameter table of said memory means;
   d) selecting at least one parameter from said parameter table which is suitable for characterizing said surface type;
   e) determining from at least one of said selected parameters from said parameter table the associated predetermined angle at which the corresponding measuring means is directed to the measurement surface;
   f) transferring said at least one selected angle to a second measuring device which comprises:
      at least one illuminating means having at least one light source, its light directed at a predetermined angle to a measurement surface which is a part of the surface to be measured;
      at least one measuring means, and receives a portion of the light reflected from measurement surface, and wherein each measuring means comprises at least one photosensor which emits an electrical measurement signal which is characteristic of the light received by said measuring means;
      at least one control and evaluation means having at least one processor means and at least one memory means, wherein said control means controls the measurement sequence and evaluates the measurement results and derives therefrom at least one parameter which characterizes said surface;
      an output means for outputting at least said at least one parameter,
      and the arranging of said measuring means of said second measuring device at said selected angle to said measurement surface;

wherein said second measuring device comprises a number of retaining means which is greater than its number of measuring means, and wherein an angle spacing between adjacent retaining means is identical, and wherein at least one measuring means is arranged on different retaining means so that the angle at which said measuring means is directed to said measurement surface is variable in discrete increments.

19. Procedure according to claim 18, wherein at least three different angles are selected from said first measuring device and transferred to said second measuring device.

20. Procedure according to claim 18, wherein an arrangement of said retaining means of said second measuring device is identical to an arrangement of said retaining means of said first measuring device.

* * * * *